Jan. 16, 1973 J. M. GARABEDIAN Plant Pat. 3,295
GRAPEVINE
Filed May 28, 1971
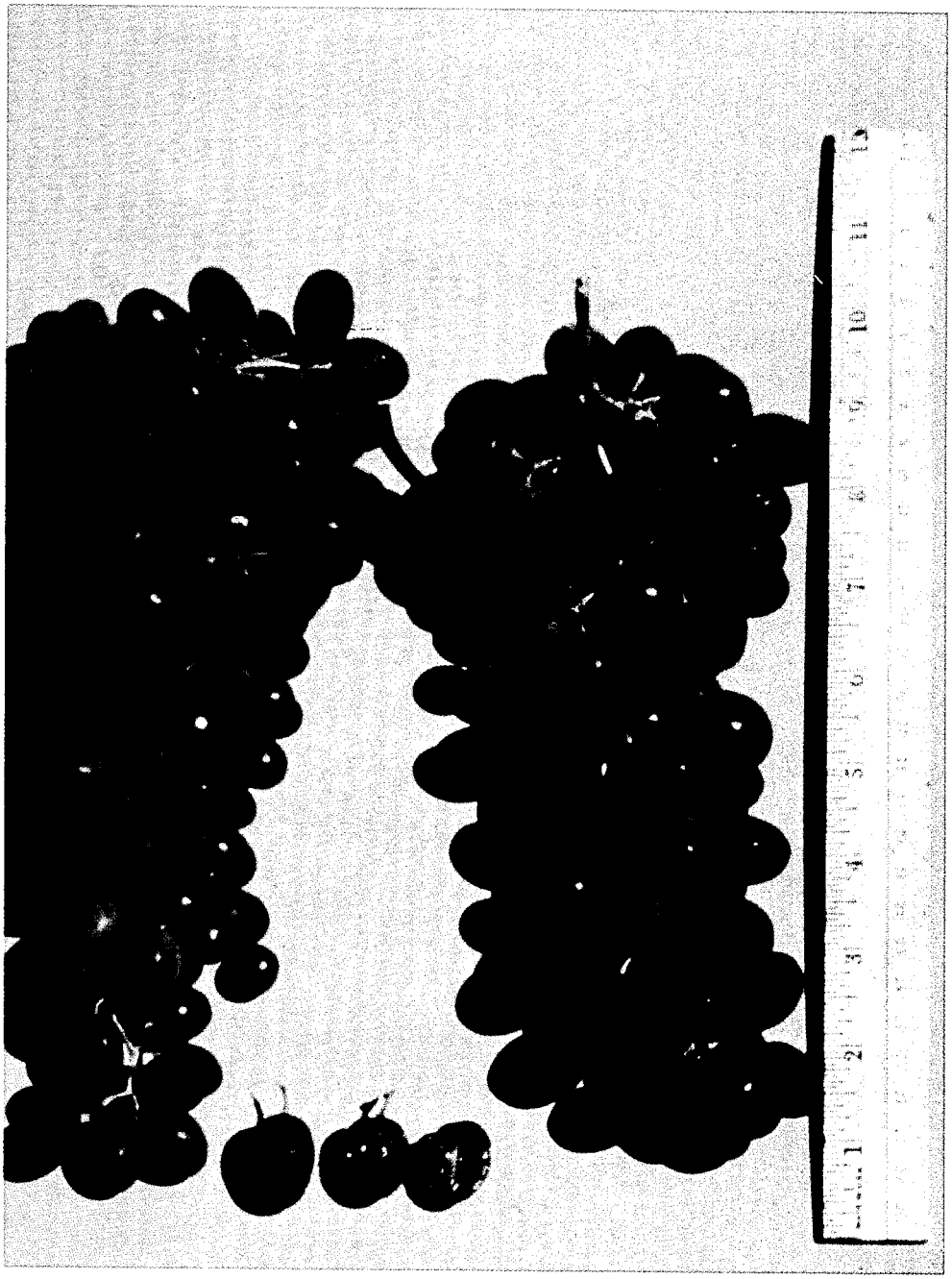
INVENTOR
John M. Garabedian
BY
Webster & Webster
ATTORNEYS United States Patent Office Plant Pat. 3,295
Patented Jan. 16, 1973

3,295

GRAPEVINE

John M. Garabedian, Fresno, Calif., assignor to Superior Farming Company

Filed May 28, 1971, Ser. No. 148,246
Int. Cl. A01h 5/03
U.S. Cl. Plt.—47 1 Claim

ABSTRACT OF THE DISCLOSURE

A vigorous, horizontally growing, hardy grapevine which is a regular and productive bearer of medium-size clusters of black, seedless grapes which ripen about seven to ten days earlier than the Black Monukka (unpatented); the individual berries of the present variety of grapevine being characterized, in comparison to said Black Monukka, by more purplish-black to black color, more ovoid-elongated shape, larger diameter, tougher and thicker skin, more looseness in the cluster, and vestigial seeds which are a darker brown color and usually having a fiber remaining attached to the seed beak.

ORIGIN OF THE VARIETY

The present variety of grapevine was originated by me as a cross between the Thompson Seedless (unpatented) and an unnamed seedling (unpatented) of the Ribier (unpatented); such origination having been accomplished on a ranch, located near Madera, Madera County, Calif., of which I am an owner. The vine which resulted from such cross was maintained by me under careful and continuing observation, and—upon bearing fruit—I recognized its new and distinctive characteristics and which classed it as a superior grape for the fresh market as well as drying for raisins.

ASEXUAL REPRODUCTION OF THE VARIETY

Subsequent to origination of the present variety of grapevine, and recognition of its advantageous characteristics, I asexually reproduced such variety by top-working the same on seeding grapevines in a vineyard on the aforesaid ranch. When grown to maturity, and in bearing, such asexual reproductions ran true to the original grapevine in all respects.

SUMMARY OF THE VARIETY

The herein claimed variety of grapevine is characterized, in comparison to the Black Monukka and which it generally resembles, by ripening of the black seedless grapes about seven to ten days earlier and by individual grape berries which are more purplish-black to black in color, more ovoid-elongated in shape, large in diameter, tougher and thicker of skin, more loose in the cluster, and with vestigial seeds of darker brown color and usually having a fiber remaining attached to the seed beak.

The herein claimed variety of grapevine is further characterized by a vine which is vigorous, horizontally growing, hardy, and a regular and productive bearer of medium-size clusters of grape berries of the type described.

BRIEF DESCRIPTION OF THE DRAWING

The drawing is an illustration, by photographic reproduction in color, of two clusters of berries, and two detached berries, one of the latter being cut into halves.

DESCRIPTION OF THE VARIETY

The botanical details of this new and distinct variety of grapevine—with color definitions (except those in common color terms) referenced to Maerz and Paul Dictionary of Color—are as follows:

Vine: Vigorous; horizontal; hardy; productive.
Trunk: Large size; medium caliber.
- *Bark.*—Loose; shreddy.
- *Color.*—New wood—Brown (6–E–9)—old wood—Grey (46–A–1).

Canes: Long to medium; numerous; medium thickness; usually straight; brown (12–C–7).
- *Nodes.*—Slightly enlarged.
- *Internodes.*—Mostly medium length.
- *Tendrils.*—Intermittent; medium thickness; long; usually trifurcated; smooth.

Flowers: Fertile.
- *Blooming period.*—Medium. Date of first bloom—May 8, 1970. Date of last bloom—May 18, 1970.
- *Stamens.*—Upright.
- *Position of flowers.*—Usually formed at 2d–7th nodes, but mostly at 3rd node.

Leaves: Large to medium; cordate; medium thick.
- *Color.*—Upper surface—Dull medium green (23–E–9); lower surface—Pale green (22–L–7).
- *Texture.*—Mostly smooth; some slightly irregular.
- *Pubescence.*—Downy—very light.
- *Lobes.*—Number—5; terminal lobe—mostly acuminate.
- *Petiolar sinus*—Medium depth; medium width.
- *Basal sinus.*—Shallow; narrow width.
- *Lateral sinus.*—Medium depth; narrow width.
- *Margin.*—Dentate.

Fruit:
- *Date of ripening.*—Sept. 7, 1970.
- *Season.*—Medium—late mid-season.
- *Keeping quality.*—Good.
- *Shipping quality.*—Good.
- *Cluster.*—Medium size: weight per cluster—8–16 ounces, average—11⅝ ounces; long; usually slender; tapering to cylindrical; regular; usually single shouldered; medium compact. Clusters per cane—2–4, average 3. Peduncle—short; medium thick. Pedicel—medium length; slender; warts usually at torus end. Blush—medium to short; greenish—opaque; vestigial seeds may adhere to brush when pulled.
- *Berries.*—Strongly adherent; usually large; uniform; usually ovoid-elongated. Color—usually black—many purplish-black (48–L–12), with thick grey (47–A–3) bloom. Skin—thick; tough; separates from pulp. Flesh—greenish, translucent; medium texture; tender; juice—medium, clear, sweet, slightly vinous, sometimes slightly sprightly; quality—good. Sacchrometer test—average—22.8% solids. Seeds—all seeds vestigial; separate from pulp easily; average number—2.2; small; short; narrow; mostly rounded; pointed; dark brown. Raphe—mostly cord-like. Chalaza—usually positioned below center; many obscure; mostly sunken. Use—fresh market; drying for raisins.

The grapevine and its fruit herein described may vary in slight detail due to climatic and soil conditions under which the variety may be grown; the present description being of the variety as grown in the Central Valley of California.

I claim:

1. A new and distinct variety of grapevine, substantially as illustrated and described, which is vigorous, horizontally growing, hardy, and a regular and productive bearer of medium-size clusters of black seedless grapes which ripen about seven to ten days earlier than the Black Monukka; the individual berries of the variety being characterized, in comparison to said Black Monukka, by more purplish-black to black color, more ovoid-elongated shape, larger diameter, tougher and thicker skin, more looseness in the cluster, and vestigial seeds which are a darker brown color.

No references cited.

ROBERT E. BAGWILL, Primary Examiner